United States Patent
Keller et al.

(10) Patent No.: US 11,618,725 B2
(45) Date of Patent: Apr. 4, 2023

(54) PROCESS TO RECOVER 3-METHYL-BUT-3-EN-1-OL

(71) Applicant: BASF SE, Ludwigshafen am Rhein (DE)

(72) Inventors: Andreas Keller, Ludwigshafen am Rhein (DE); Martin Kamasz, Ludwigshafen am Rhein (DE); Gabriele Gralla, Ludwigshafen am Rhein (DE); Roland Minges, Minden (DE); Bernhard Brunner, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 9 days.

(21) Appl. No.: 17/441,420

(22) PCT Filed: Mar. 18, 2020

(86) PCT No.: PCT/EP2020/057363
§ 371 (c)(1),
(2) Date: Sep. 21, 2021

(87) PCT Pub. No.: WO2020/187953
PCT Pub. Date: Sep. 24, 2020

(65) Prior Publication Data
US 2022/0169586 A1    Jun. 2, 2022

(30) Foreign Application Priority Data
Mar. 21, 2019  (EP) ..................................... 19164238

(51) Int. Cl.
*C07C 29/38*   (2006.01)
*C07C 29/74*   (2006.01)
*C07C 29/80*   (2006.01)

(52) U.S. Cl.
CPC .............. *C07C 29/38* (2013.01); *C07C 29/74* (2013.01); *C07C 29/80* (2013.01)

(58) Field of Classification Search
CPC .......... C07C 29/38; C07C 29/74; C07C 29/80
See application file for complete search history.

(56) References Cited

U.S. PATENT DOCUMENTS

| | | | | |
|---|---|---|---|---|
| 3,574,773 A | * | 4/1971 | Mueller | ................ C07C 33/025 585/609 |
| 4,079,088 A | * | 3/1978 | Wall | ........................ C07C 29/36 568/904 |
| 4,139,556 A | | 2/1979 | Wall | |

FOREIGN PATENT DOCUMENTS

DE    1279014 B  * 10/1968  ............. C07C 29/38

OTHER PUBLICATIONS

DE1279014B, Mueller, H., et al., Process for preparing alkenols, English translation, 6 pages (Year: 1968).*
European Search Report for EP Patent Application No. 19164238.8, dated Sep. 6, 2019, 3 pages.
International Search Report and Written Opinion received for PCT Patent Application No. PCT/EP2020/057363, dated Jun. 26, 2020, 8 pages.

* cited by examiner

*Primary Examiner* — Yate' K Cutliff
(74) *Attorney, Agent, or Firm* — Faegre Drinker Biddle & Reath LLP

(57) ABSTRACT

The presently claimed invention relates to a process for the recovery of 3-methyl-3-buten--ol from a stream comprising (Z)-3-methylpent-2-ene-1,5-diol, (E)-3-methylpent-2-ene-,5-diol and 3-methylenepentane-1,5-diol by treating the stream with isobutene and water.

15 Claims, No Drawings

PROCESS TO RECOVER 3-METHYL-BUT-3-EN-1-OL

CROSS-REFERENCE TO RELATED APPLICATIONS

This application is a national stage application (under 35 U.S.C. § 371) of PCT/EP2020/057363, filed Mar. 18, 2020, which claims benefit of European Application No. 19164238.8, filed Mar. 21, 2019, both of which are incorporated herein by reference in their entirety.

FIELD OF THE INVENTION

The presently claimed invention relates to a process for the recovery of 3-methyl-3-buten-1-ol from a stream comprising (Z)-3-methylpent-2-ene-1,5-diol, (E)-3-methylpent-2-ene-1,5-diol and 3-methylenepentane-1,5-diol by treating the stream with isobutene and water.

BACKGROUND OF THE INVENTION

The synthesis of 3-methyl-3-buten-1-ol from a reaction of 2-methylprop-1-ene and formaldehyde is well known from the literature and used on an industrial scale. 3-Methyl-3-buten-1-ol is an important starting material for the manufacture of polymers, resins, plasticizers and synthetic lubricants, and is also used as chemical intermediate in the production of materials such as citral.

It is also well known in the art that a mixture of 3-methylene-1,5-pentanediol and the two geometric isomers of 3-methyl-2-pentene-1,5-diol is obtained during the synthesis of apart from 3-methyl-3-buten-1-ol.

U.S. Pat. No. 4,079,088 describes a process for producing 3-methyl-3-buten-1-ol from a mixture of (E/Z)-3-methyl-2-pentene-1,5-diol and 3-methylene-1,5-pentanediol by heating the mixture of diols at a temperature between 200° C. and 450° C. in the presence of isobutene. However, such method results in poor yields of 3-methyl-3-buten-1-ol ranging from 10% to 32% (by mol) only. Thus, the process is especially unsuitable for a large-scale production of 3-methyl-3-buten-1-ol.

It is accordingly an object of the presently claimed invention to counter the disadvantages described in the prior art and provide an improved process for the synthesis of 3-methyl-3-buten-1-ol which is easy to carry out industrially and leads to high overall selectivity and yields of 3-methyl-3-buten-1-ol.

SUMMARY OF THE INVENTION

It was surprisingly found that the addition of water in the reaction of the mixture of diols with isobutene results in an increased yield of the recovered 3-methyl-but-3-en-1-ol in the range of 43% to 47% (by mol). Furthermore, the selectivity of the recovered 3-methyl-but-3-en-1-ol was also improved.

Thus, in one aspect, the presently claimed invention relates to a method for recovery of 3-methyl-but-3-en-1-ol comprising at least the steps of a) contacting a stream comprising (Z)-3-methylpent-2-ene-1,5-diol, (E)-3-methylpent-2-ene-1,5-diol and 3-methylenepentane-1,5-diol with isobutene and water to obtain a mixture, b) heating the mixture obtained in step a) to a temperature in the range of ≥200° C. to ≤450° C. to obtain a treated mixture comprising 3-methyl-but-3-en-1-ol; and c) recovering 3-methyl-but-3-en-1-ol from the treated mixture obtained in step b).

In another aspect, the presently claimed invention is directed to a process for providing the stream comprising (Z)-3-methylpent-2-ene-1,5-diol, (E)-3-methylpent-2-ene-1,5-diol and 3-methylenepentane-1,5-diol, wherein the process comprises at least the steps of:

A) reacting 2-methylprop-1-ene and formaldehyde to obtain a mixture comprising at least 3-methyl-but-3-en-1-ol, formaldehyde, methanol, water, (Z)-3-methylpent-2-ene-1,5-diol, (E)-3-methylpent-2-ene-1,5-diol and 3-methylenepentane-1,5-diol;

B) separating the mixture obtained in step A) into an organic phase comprising at least 3-methyl-but-3-en-1-ol, (Z)-3-methylpent-2-ene-1,5-diol, (E)-3-methylpent-2-ene-1,5-diol and 3-methylenepentane-1,5-diol and an aqueous phase comprising water and ≤10 wt. % 3-methyl-but-3-en-1-ol, preferably ≥2.0 to ≤10 wt. % 3-methyl-but-3-en-1-ol, based on the total weight of the aqueous phase; and C) subjecting the organic phase obtained in step B) to a temperature in the range of ≥120° C. to ≤160° C. to obtain 3-methyl-but-3-en-1-ol and the stream comprising (Z)-3-methylpent-2-ene-1,5-diol, (E)-3-methylpent-2-ene-1,5-diol and 3-methylenepentane-1,5-diol.

In yet another aspect, the presently claimed invention is also directed to a process for the production of 3-methyl-but-3-en-1-ol, wherein the process comprises at least the steps of:

AA) reacting 2-methylprop-1-ene and formaldehyde to obtain a mixture comprising at least 3-methyl-but-3-en-1-ol, formaldehyde, methanol, water, (Z)-3-methylpent-2-ene-1,5-diol, (E)-3-methylpent-2-ene-1,5-diol and 3-methylenepentane-1,5-diol;

BB) separating the mixture obtained in step AA) into an organic phase comprising at least 3-methyl-but-3-en-1-ol, (Z)-3-methylpent-2-ene-1,5-diol, (E)-3-methylpent-2-ene-1,5-diol and 3-methylenepentane-1,5-diol and an aqueous phase comprising water and ≤10 wt. % 3-methyl-but-3-en-1-ol, preferably ≥2.0 to ≤10 wt. % 3-methyl-but-3-en-1-ol, based on the total weight of the aqueous phase;

CC) subjecting the organic phase obtained in step BB) to a temperature in the range of ≥120° C. to ≤160° C. to obtain 3-methyl-but-3-en-1-ol and the stream comprising (Z)-3-methylpent-2-ene-1,5-diol, (E)-3-methylpent-2-ene-1,5-diol and 3-methylenepentane-1,5-diol; and DD) combining 3-methyl-but-3-en-1-ol obtained in step CC) with 3-methyl-but-3-en-1-ol obtained by the recovery process according to the presently claimed invention to obtain combined 3-methyl-but-3-en-1-ol.

DETAILED DESCRIPTION OF THE INVENTION

The following detailed description is merely exemplary in nature and is not intended to limit the presently claimed invention or the application and uses of the presently claimed invention. Furthermore, there is no intention to be bound by any theory presented in the preceding technical field, background, summary or the following detailed description.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

Furthermore, the terms "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the subject matter described herein are capable of operation in other sequences than described or illustrated herein. In case the terms "(A)", "(B)" and "(C)" or AA), BB) and CC) or "(a)", "(b)", "(c)", "(d)", "(i)", "(ii)" etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

In the following passages, different aspects of the subject matter are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" or "preferred embodiment" means that a particular feature, structure or characteristic described in connection with the embodiment is included in at least one embodiment of the presently claimed invention. Thus, appearances of the phrases "in one embodiment" or "In a preferred embodiment" or "in a preferred embodiment" in various places throughout this specification are not necessarily all referring to the same embodiment but may refer. Furthermore, the features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the subject matter, and form different embodiments, as would be understood by those in the art. For example, in the appended claims, any of the claimed embodiments are used in any combination.

Furthermore, the ranges defined throughout the specification include the end values as well, i.e. a range of 1 to 10 implies that both 1 and 10 are included in the range. For the avoidance of doubt, the applicant shall be entitled to any equivalents according to applicable law.

In one embodiment, the presently claimed invention provides a process for providing the stream comprising (Z)-3-methylpent-2-ene-1,5-diol, (E)-3-methylpent-2-ene-1,5-diol and 3-methylenepentane-1,5-diol, wherein the process comprises at least the steps of:

A) reacting 2-methylprop-1-ene and formaldehyde to obtain a mixture comprising at least 3-methyl-but-3-en-1-ol, formaldehyde, methanol, water, (Z)-3-methylpent-2-ene-1,5-diol, (E)-3-methylpent-2-ene-1,5-diol and 3-methylenepentane-1,5-diol;

B) separating the mixture obtained in step A) into an organic phase comprising at least 3-methyl-but-3-en-1-ol, (Z)-3-methylpent-2-ene-1,5-diol, (E)-3-methylpent-2-ene-1,5-diol and 3-methylenepentane-1,5-diol and an aqueous phase comprising water and ≤10 wt. % 3-methyl-but-3-en-1-ol, preferably ≥2.0 to ≤10 wt. % 3-methyl-but-3-en-1-ol, based on the total weight of the aqueous phase; and C) subjecting the organic phase obtained in step B) to a temperature in the range of ≥120° C. to ≤160° C. to obtain 3-methyl-but-3-en-1-ol and the stream comprising (Z)-3-methylpent-2-ene-1,5-diol, (E)-3-methylpent-2-ene-1,5-diol and 3-methylenepentane-1,5-diol.

The formaldehyde used in step A) is used in gaseous form, in polymeric form or in the form of an aqueous solution. Though formaldehyde may be used as it is, formaldehyde having been dissolved in a solvent can also be used. Though the solvent that dissolves formaldehyde therein is not particularly limited, it is preferably water from the standpoint of easy availability.

In a preferred embodiment, aqueous formaldehyde is used. In addition, from the viewpoint of volumetric efficiency, it is preferred that the concentration of formaldehyde is higher. However, when the concentration of formaldehyde is too high, a problem of deposition is caused, resulting in making its handling difficult. The concentration of the formaldehyde solution is preferably 10 to 70 wt. %, more preferably 30 to 60 wt. %, yet more preferably 35 wt. % to 55 wt. %.

In another preferred embodiment, 1.0 to 60.0 mol, more preferably 2.0 to 30.0 mol, yet more preferably 3.0 to 30.0 mol, most preferably 2.0 to 15.0 mol, and in particular 3.0 to 15.0 mol of 2-methylprop-1-ene to 1.0 mol formaldehyde are used in step A).

In another embodiment, the step A) is carried out in the presence or absence of a solvent. In a preferred embodiment, the step a) is carried out in the absence of any solvent.

In another embodiment, the step A) is carried out in the presence or absence of an amine. In a preferred embodiment, the step A) is carried out in the presence of an amine. The amine is selected from the group consisting of trimethylamine, dimethylamine, triethylamine, diethylamine, triisopropylamine, diisopropylamine, 1-propylamine, butan-2-amine, methylpropan-2-amine, ethane-1,2-diamine, urotropine, pyridine and piperidine. In a more preferred embodiment, the amine is urotropine.

In another preferred embodiment, the reaction temperature in step A) is in the range of 200° C. to 350° C., preferably in the range of 220° C. to 300° C., more preferably in the range of 240° C. to 280° C.

In another preferred embodiment, the reaction pressure in step A) is in the range of 200 bar to 300 bar, preferably in the range of 50 bar to 280 bar, more preferably in the range of 100 bar to 280 bar, yet more preferably in the range of 150 bar to 250 bar.

In a preferred embodiment, the reaction of step A) is carried out in a batch mode, semi-batch mode or continuous mode. The step A) is more preferably carried out in the continuous mode.

In a preferred embodiment, a mixed solution containing 2-methylprop-1-ene and the aqueous formaldehyde solution in predetermined ratios is fed into a reaction vessel which is heated at a predetermined temperature. The reaction pressure is regulated and is kept at a predetermined pressure. The aforementioned mixed solution is allowed to remain within the reaction vessel for a predetermined time of about 0.025 hours to about 5.0 hours, preferably 0.05 hours to about 2.0 hours, more preferably for about 0.05 hours to about 1.5 hours to obtain a reaction mixture. The reaction mixture is cooled.

In another preferred embodiment, the mixture comprising 3-methyl-but-3-en-1-ol, formaldehyde, methanol, water, (Z)-3-methylpent-2-ene-1,5-diol, (E)-3-methylpent-2-ene-1, 5-diol and 3-methylenepentane-1,5-diol is obtained from step A). The mixture obtained from step A) further comprises 3-methyl-but-3-enyl formate and 3-methyl-but-2-enal. The condensates of the mixture obtained from step A) consist of two phases, namely the upper organic phase and the lower aqueous phase. The mixture obtained from step A) is separated in step B) into an organic phase comprising at least 3-methyl-but-3-en-1-ol, (Z)-3-methylpent-2-ene-1,5-diol, (E)-3-methylpent-2-ene-1,5-diol and 3-methylenepentane-1,5-diol and an aqueous phase comprising water and ≤10 wt. % 3-methyl-but-3-en-1-ol, preferably ≥2.0 to ≤10 wt. % 3-methyl-but-3-en-1-ol, based on the total weight of the aqueous phase.

The organic phase obtained in step B) is subjected to a temperature in the range of ≥120° C. to ≤160° C. in a distillation column to separate a light boiling fraction comprising water and methanol from a high boiling fraction comprising 3-methyl-but-3-en-1-ol, (Z)-3-methylpent-2-ene-1,5-diol, (E)-3-methylpent-2-ene-1,5-diol and 3-methylenepentane-1,5-diol.

In another preferred embodiment, the organic phase obtained in step B) is subjected to a temperature in the range of ≥120° C. to ≤160° C. at the pressure in the range of ≥50 to ≤300 mbar to obtain 3-methyl-but-3-en-1-ol and the stream comprising (Z)-3-methylpent-2-ene-1,5-diol, (E)-3-methylpent-2-ene-1,5-diol and 3-methylenepentane-1,5-diol.

In another embodiment, the aqueous phase obtained in step B) comprises at least water and ≤10 wt. % 3-methyl-but-3-en-1-ol, preferably ≥2.0 to ≤10 wt. % 3-methyl-but-3-en-1-ol, based on the total weight of an aqueous phase.

In yet another embodiment, the aqueous phase from step B) is combined with the light boiling fraction comprising water and methanol of step C). The 3-methyl-but-3-en-1-ol is isolated from the combined aqueous phase from step B) and the light boiling fraction comprising water and methanol of step C) by distillation.

In yet another embodiment, the high boiling fraction comprising at least 3-methyl-but-3-en-1-ol, (Z)-3-methylpent-2-ene-1,5-diol, (E)-3-methylpent-2-ene-1,5-diol and 3-methylenepentane-1,5-diol obtained in step B) is subjected to a temperature in the range of ≥120° C. to ≤165° C. in a distillation column at the pressure is in the range of ≥50 to ≤150 mbar to obtain 3-methyl-but-3-en-1-ol and the stream comprising (Z)-3-methylpent-2-ene-1,5-diol, (E)-3-methylpent-2-ene-1,5-diol and 3-methylenepentane-1,5-diol.

In one embodiment, the presently claimed invention provides a method for recovery of 3-methyl-but-3-en-1-ol comprising at least the steps of
 a) contacting a stream comprising (Z)-3-methylpent-2-ene-1,5-diol, (E)-3-methylpent-2-ene-1,5-diol and 3-methylenepentane-1,5-diol with isobutene and water to obtain a mixture,
 b) heating the mixture obtained in step a) to a temperature in the range of ≥200° C. to ≤450° C. to obtain a treated mixture comprising 3-methyl-but-3-en-1-ol; and
 c) recovering 3-methyl-but-3-en-1-ol from the treated mixture obtained in step b).

In a preferred embodiment, the steps a) to c) are carried out in a batch mode, a semi-batch mode and a continuous mode. In more preferred embodiment, the steps a) to c) are carried out in a continuous mode. In another preferred embodiment, the steps a) to c) are carried out simultaneously.

In a preferred embodiment, the stream comprising (Z)-3-methylpent-2-ene-1,5-diol, (E)-3-methylpent-2-ene-1,5-diol and 3-methylenepentane-1,5-diol is subjected to a temperature in the range of ≥115° C. to ≤170° C. in a distillation column at the pressure is in the range of ≥1 to ≤10 mbar to obtain the stream comprising (Z)-3-methylpent-2-ene-1,5-diol, (E)-3-methylpent-2-ene-1,5-diol and 3-methylenepentane-1,5-diol in an amount in the range of ≥75.0 wt. % to ≤99.0 wt. %, more preferably in the range of ≥80.0 wt. % to ≤95.0 wt. %, based on the total weight of the stream.

In another preferred embodiment, the stream comprises (Z)-3-methylpent-2-ene-1,5-diol in an amount in the range of ≥15 wt. % to ≤30 wt. %, (E)-3-methylpent-2-ene-1,5-diol in an amount in the range of ≥15 wt. % to ≤30 wt. % and 3-methylenepentane-1,5-diol in an amount in the range of ≥35 wt. % to ≤55 wt. %, each based on the total weight of the stream.

In yet another preferred embodiment, the stream further comprises (Z)-3-methylpent-2-ene-1,5-diol in an amount in the range of ≥15 wt. % to ≤30 wt. %, (E)-3-methylpent-2-ene-1,5-diol in an amount in the range of ≥15 wt. % to ≤30 wt. % and 3-methylenepentane-1,5-diol in an amount in the range of ≥35 wt. % to ≤55 wt. %, 3-methylpent-4-ene-1,3-diol in an amount of ≤5 wt. %, 3-methylbutane-1,3-diol in an amount of ≤3 wt. %, 3(2-hydroxyethyl)pent-2-ene-1,5-diol in an amount of ≤2 wt. % whereby the amount of wt. % are based on the total weight of the stream and add up to 100 wt. %.

In a preferred embodiment, the isobutene is added in step a) in an amount in the range of ≥75 wt. % to ≤90 wt. %, more preferably in the range of ≥80 to ≤90 wt. %, based on the total weight of the stream.

In yet another preferred embodiment, the water is added in step a) in an amount in the range of ≥5 wt. % to ≤70 wt. %, more preferably in the range of ≥7 wt. % to ≤65 wt. %, based on the total weight of the stream comprising (Z)-3-methylpent-2-ene-1,5-diol, (E)-3-methylpent-2-ene-1,5-diol and 3-methylenepentane-1,5-diol in an amount in the range of ≥75.0 wt. % to ≤99.0 wt. %.

In a preferred embodiment, the mixture obtained in step a) is heated to a temperature in the range of ≥200° C. to ≤450° C., more preferably in the range of ≥220° C. to ≤440° C., at a pressure in the range of ≥60 bar to ≤260 bar, to obtain a treated mixture comprising 3-methyl-but-3-en-1-ol. In yet another preferred embodiment, the mixture obtained in step a) is heated to a temperature in the range of ≥200° C. to ≤450° C. at a pressure in the range of ≥60 bar to ≤260 bar to obtain a treated mixture further comprising (Z)-3-methylpent-2-ene-1,5-diol, (E)-3-methylpent-2-ene-1,5-diol and 3-methylenepentane-1,5-diol in an amount in the range of ≥12.0 wt. % to ≤20.0 wt. %.

In yet another preferred embodiment, the step a) is carried out over a period of 0.25 h to 5 h, more preferably over a period of 0.5 h to 4 h, yet more preferably over a period of 1.0 h to 3 h, in particular over a period of 1.0 h to 2.5 h.

In another preferred embodiment, the step c) comprises at least the steps of
 A') separating the treated mixture obtained in step b) into an organic phase comprising at least ≥60 wt. % 3-methyl-but-3-en-1-ol methanol, based on the total weight of the organic phase, and an aqueous phase comprising water and ≤10 wt. % 3-methyl-but-3-en-1-ol, preferably ≥2.0 to ≤10 wt. % 3-methyl-but-3-en-1-ol, based on the total weight of the aqueous phase; and
 B') subjecting the organic phase obtained in step A') to a temperature in the range of ≥120° C. to ≤160° C.

In yet another preferred embodiment, the treated mixture further comprising (Z)-3-methylpent-2-ene-1,5-diol, (E)-3-methylpent-2-ene-1,5-diol and 3-methylenepentane-1,5-diol in an amount in the range of ≥12.0 wt. % to ≤20.0 wt. % is recycled back to step A) or step B).

In one embodiment, the presently claimed invention provides a process for the production of 3-methyl-but-3-en-1-ol, wherein the process comprises at least the steps of:
  AA) reacting 2-methylprop-1-ene and formaldehyde to obtain a mixture comprising at least 3-methyl-but-3-en-1-ol, formaldehyde, methanol, water, (Z)-3-methylpent-2-ene-1,5-diol, (E)-3-methylpent-2-ene-1,5-diol and 3-methylenepentane-1,5-diol;
  BB) separating the mixture obtained in step AA) into an organic phase comprising at least 3-methyl-but-3-en-1-ol, (Z)-3-methylpent-2-ene-1,5-diol, (E)-3-methylpent-2-ene-1,5-diol and 3-methylenepentane-1,5-diol and an aqueous phase comprising water and ≤10 wt. % 3-methyl-but-3-en-1-ol, preferably ≥2.0 to ≤10 wt. % 3-methyl-but-3-en-1-ol, based on the total weight of the aqueous phase;
  CC) subjecting the organic phase obtained in step BB) to a temperature in the range of ≥120° C. to ≤160° C. to obtain 3-methyl-but-3-en-1-ol and the stream comprising (Z)-3-methylpent-2-ene-1,5-diol, (E)-3-methylpent-2-ene-1,5-diol and 3-methylenepentane-1,5-diol; and
  DD) combining 3-methyl-but-3-en-1-ol obtained in step CC) with 3-methyl-but-3-en-1-ol obtained by the recovery process according to the presently claimed invention to obtain combined 3-methyl-but-3-en-1-ol.

In a preferred embodiment, the 3-methyl-but-3-en-1-ol recovered in step c) is combined with the 3-methyl-but-3-en-1-ol obtained from step CC). The combined 3-methyl-but-3-en-1-ol is subjected to a purification method to obtain purified combined 3-methyl-but-3-en-1-ol.

In another preferred embodiment, the purification method is selected from filtration, evaporation, distillation and chromatography, more preferably the purification method is distillation.

In yet another preferred embodiment, the distillation for the purification of the combined 3-methyl-but-3-en-1-ol is carried out at a temperature in the range of ≥120° C. to ≤160° C. to obtain purified 3-methyl-but-3-en-1-ol. The purified 3-methyl-but-3-en-1-ol has a purity of ≥98.0 wt. %.

In the following, there is provided a list of embodiments to further illustrate the present disclosure without intending to limit the disclosure to the specific embodiments listed below.

1. A method for recovery of 3-methyl-but-3-en-1-ol comprising at least the steps of
  a) contacting a stream comprising (Z)-3-methylpent-2-ene-1,5-diol, (E)-3-methylpent-2-ene-1,5-diol and 3-methylenepentane-1,5-diol with isobutene and water to obtain a mixture,
  b) heating the mixture obtained in step a) to a temperature in the range of ≥200° C. to ≤450° C. to obtain a treated mixture comprising 3-methyl-but-3-en-1-ol; and
  c) recovering 3-methyl-but-3-en-1-ol from the treated mixture obtained in step b).
2. The method according to embodiment 1, wherein the method is a continuous method.
3. The method according to embodiment 1 or 2, wherein the steps a) to c) are carried out simultaneously.
4. The method according to embodiment 1, wherein the stream comprises (Z)-3-methylpent-2-ene-1,5-diol, (E)-3-methylpent-2-ene-1,5-diol and 3-methylenepentane-1,5-diol in an amount in the range of ≥75.0 wt. % to ≤99.0 wt. %, based on the total weight of the stream.
5. The method according to any of embodiments 1 to 4, wherein the stream comprises
  (Z)-3-methylpent-2-ene-1,5-diol in an amount in the range of ≥15 wt. % to ≤30 wt. %,
  (E)-3-methylpent-2-ene-1,5-diol in an amount in the range of ≥15 wt. % to ≤30 wt. % and
  3-methylenepentane-1,5-diol in an amount in the range of ≥35 wt. % to ≤55 wt. %, each based on the total weight of the stream.
6. The method according to embodiment 1, wherein in step a) the isobutene is added in an amount in the range of ≥75 wt. % to ≤90 wt. %, based on the total weight of the stream.
7. The method according to embodiment 1, wherein in step a) the water is added in an amount in the range of ≥5 wt. % to ≤70 wt. %, based on the total weight of the stream according to embodiment 1.
8. The method according to embodiment 1, wherein the step b) further comprises heating the mixture at a pressure in the range of ≥60 bar to ≤260 bar.
9. The method according to embodiment 1, wherein the step c) comprises at least the steps of
  A') separating the treated mixture obtained in step b) into an organic phase comprising at least ≥60 wt. % 3-methyl-but-3-en-1-ol methanol, based on the total weight of the organic phase, and an aqueous phase comprising water and ≤10 wt. % 3-methyl-but-3-en-1-ol, preferably ≥2.0 to ≤10 wt. % 3-methyl-but-3-en-1-ol, based on the total weight of the aqueous phase; and
  B') subjecting the organic phase obtained in step A') to a temperature in the range of ≥120° C. to ≤160° C.
10. The method according to any one of embodiments 1 to 9, wherein the stream of step a) is obtained by a process comprising at least the steps of:
  A) reacting 2-methylprop-1-ene and formaldehyde to obtain a mixture comprising at least 3-methyl-but-3-en-1-ol, formaldehyde, methanol, water, (Z)-3-methylpent-2-ene-1,5-diol, (E)-3-methylpent-2-ene-1,5-diol and 3-methylenepentane-1,5-diol;
  B) separating the mixture obtained in step A) into an organic phase comprising at least 3-methyl-but-3-en-1-ol, (Z)-3-methylpent-2-ene-1,5-diol, (E)-3-methylpent-2-ene-1,5-diol and 3-methylenepentane-1,5-diol and an aqueous phase comprising water and ≤10 wt. % 3-methyl-but-3-en-1-ol, based on the total weight of the aqueous phase; and
  C) subjecting the organic phase obtained in step B) to a temperature in the range of ≥120° C. to ≤160° C. to obtain 3-methyl-but-3-en-1-ol and the stream comprising (Z)-3-methylpent-2-ene-1,5-diol, (E)-3-methylpent-2-ene-1,5-diol and 3-methylenepentane-1,5-diol.
11. The process according to embodiment 10, wherein in step A) the temperature is in the range of ≥200° C. to ≤350° C.
12. The process according to embodiment 10, wherein in step A) the pressure is in the range of ≥200 bar to ≤300 bar.
13. The process according to embodiment 10, wherein in step C) the pressure is in the range of ≥50 to ≤300 mbar.
14. A process for the production of 3-methyl-but-3-en-1-ol comprising the step of combining 3-methyl-but-3-en-1-ol obtained by the method according to embodiment 10 with 3-methyl-but-3-en-1-ol obtained by the method according to any of embodiments 1 to 9 to obtain combined 3-methyl-but-3-en-1-ol.

15. The process according to embodiment 14, wherein the process further comprises the step of subjecting the combined 3-methyl-but-3-en-1-ol to a purification method to obtain combined 3-methyl-but-3-en-1-ol of a purity ≥98.0 wt. %.
16. The process according to embodiment 15, wherein the purification method is distillation.

Having described the invention, a further understanding can be obtained by reference to certain specific examples which are provided herein for the purposes of illustration only. The examples are not intended to be limiting unless otherwise specified.

EXAMPLES

The gas chromatography analysis in each of the Examples was performed under the following conditions.
Apparatus: Agilent 7890B
Column used: DB Wax 30 m, inner diameter 0.32 mm, film thickness 0.25 μm
Analysis conditions: 50° C., 5 minutes isotherm—heating rate 6° C./min to 230° C.—230° C., 30 minutes isotherm Example 1a 2-Methylprop-1-ene (2053 g), aqueous formaldehyde (200 g; 50 wt. %) and 1.4 g urotropine were placed in an autoclave. The autoclave was sealed, stirred and heated to 270° C. and thus the internal pressure rose to 100 bar. The autoclave was pressurized with nitrogen to 250 bar. The reaction mixture was stirred at 270° C. and 250 bar for 1 h. The reaction mixture was cooled to 25° C. and the pressure was released. The 2-methylprop-1-ene stream was collected, water was separated and 2-methylprop-1-ene recycled. The liquid reaction mixture was weighted and analyzed.

Organic Upper Phase: 370 g

| | |
|---|---|
| 69% = 255 g | 3-methyl-but-3-en-1-ol |
| 0.9% = 3.3 g | formaldehyde |
| 20.8% = 77 g | water |
| 2% = 7.4 g | methanol |
| 1.1% = 4.1 g | 3-methyl-but-3-en-1-yl formate |
| 1.2% = 4.4 | 3-methyl-but-2-enal |
| 5% = 5.5 g | mixture of C6-diols = (Z)-3-methylpent-2-ene-1,5-diol, (E)-3-methylpent-2-ene-1,5-diol and 3-methylene-pentane-1,5-diol |

Aqueous Lower Phase: 29 g

| | |
|---|---|
| 8% = 2.3 g | 3-methyl-but-3-en-1-ol |
| 4% = 1.16 g | methanol |
| 2% = 0.56 g | side products |
| 86% = 24.9 g | water |

Example 1b

Continuous Process

In a continuous stirred 50 ml autoclave 100 g/h isobutene and a premixed solution of 9.2 g of aqueous formaldehyde (49)+0.012 g of urotropine were added. The autoclave was operated at a temperature of 270° C. and a pressure of 240-250 bar. The reactor outlet was cooled to 150° C. and feeded into a continuous distillation, which was operated at a pressure of 6 bar and a sump temperature of 155-160° C. The isobutene was removed as distillate head stream and after phase separation to remove the aqueous phase, the isobutene was reused in the synthesis. Analysis by GC chromatography (wt. %) of the sump stream revealed the following composition:
3-methyl-but-3-en-1-ol=66.6%
methanol=2.2%
3-methyl-but-3-en-1-yl formate=1.04%
3-methyl-but-2-enal=1.1%
mixture of C6-diols=(Z)-3-methylpent-2-ene-1,5-diol, (E)-3-methylpent-2-ene-1,5-diol, 3-methylenepentane-1,5-diol=4.9%.

For the isolation and purification of 3-methyl-but-3-en-1-ol, the sump stream was transferred into further distillation steps.

General Method for the Purification of 3-methyl-but-3-en-1-ol

Distillation 1: Use was made of a continuous distillation column and the reactor outlet of Example 1 of the reaction was distilled at a pressure of 1013 mbar with a sump temperature of 130-135° C. and a head temperature of 93-96° C. The reflux ratio for the distillate stream was adjusted to 5:1.

Water, 3-methyl-but-3-en-1-yl formate, methanol and other low boilers were removed with the distillate head stream.

Distillation 2: The sump stream of distillation 1 with 3-methyl-but-3-en-1-ol, 3-methyl-but-2-enal (Z)-3-methylpent-2-ene-1,5-diol, (E)-3-methylpent-2-ene-1,5-diol and 3-methylenepentane-1,5-diol was purified in a distillation column at pressure of 120 mbar with a sump temperature of 160-165° C. and a head temperature of 75° C.-80° C. to obtain ≥98.0% pure 3-methyl-but-3-en-1-ol and a stream comprising (Z)-3-methylpent-2-ene-1,5-diol, (E)-3-methylpent-2-ene-1,5-diol and 3-methylenepentane-1,5-diol.

Distillation 3 (short-path distillation): The stream comprising (Z)-3-methylpent-2-ene-1,5-diol, (E)-3-methylpent-2-ene-1,5-diol and 3-methylenepentane-1,5-diol was fed into a distillation apparatus with a distillation bridge.

The distillation was operated at a pressure of 5 mbar with a sump temperature of 130-170° C.

At a condensation temperature of 110° C. to 140° C. a stream comprising (Z)-3-methylpent-2-ene-1,5-diol, (E)-3-methylpent-2-ene-1,5-diol and 3-methylenepentane-1,5-diol in an amount in the range of ≥75.0 wt. % to ≤90 wt. %, based on the total weight of the stream that was obtained. The stream was used without further purification in Example 2.

A stream comprising (Z)-3-methylpent-2-ene-1,5-diol, (E)-3-methylpent-2-ene-1,5-diol and 3-methylenepentane-1,5-diol was contacted with isobutene and was treated as illustrated in the examples 2a and 2b. The reactions were performed in a 300 ml steel autoclave with a glas inliner, equipped with a stirrer, gas injection pipes for isobutene/nitrogene, temperature and pressure control. The reaction mixture was analyzed by gas chromatography with an internal standard and wt.-% calibration.

The reactor outlet of examples 2a/b was used in distillation 1 and the 3-methyl-but-3-en-1-ol was isolated in distillation 2.

Example 2

Process for the Recovery of 3-methyl-but-3-en-1-ol in the Presence of Isobutene and Water a) An autoclave (300 ml) was charged with 15.0 g of a (Z)-3-methylpent-2-ene-1,5-diol, (E)-3-methylpent-2- ene-1,5-diol and 3-methylenepentane-1,5-diol mixture (83 wt. %), 0.02 g urotropine, 3.75 g water and 90.0 g of isobutene. The autoclave was sealed, heated to 270° C. and stirred for 2 h at 270° C. and a pressure of 196 bar. The autoclave was cooled to 25° C. and relaxed to atmospheric pressure. The liquid single-phase residue (21.0 g) was isolated from an autoclave. Analysis by GC chromatography (wt. %) revealed the following composition:
Methanol—1.1%,
3-methyl-but-3-en-1-ol—40.5%,
(Z)-3-methylpent-2-ene-1,5-diol,
(E)-3-methylpent-2-ene-1,5-diol and
3-methylenepentane-1,5-diol mixture—14.6%.
Conversion of diol mixture—75%
Yield of 3-methyl-but-3-en-1-ol—46.1%
Selectivity of 3-methyl-but-3-en-1-ol—61.2%.

b) An autoclave (300 ml) was charged with 15.0 g of a (Z)-3-methylpent-2-ene-1,5-diol, (E)-3-methylpent-2-ene-1,5-diol and 3-methylenepentane-1,5-diol mixture (83 wt. %), 0.02 g urotropine, 3.75 g water and 90.0 g of isobutene. The autoclave was sealed, heated to 270° C. and stirred for 2 h at 270° C. and a pressure of 190 bar. The autoclave was cooled to 25° C. and relaxed to atmospheric pressure. The liquid single-phase residue (21.2 g) was isolated from an autoclave. Analysis by GC chromatography (wt. %) revealed the following composition:
Methanol—1.1%,
3-methyl-but-3-en-1-ol—39.4%,
(Z)-3-methylpent-2-ene-1,5-diol,
(E)-3-methylpent-2-ene-1,5-diol and
3-methylenepentane-1,5-diol mixture—13.6%.
Conversion of diol mixture—77%
Yield of 3-methyl-but-3-en-1-ol—45.3%
Selectivity of 3-methyl-but-3-en-1-ol—58.9%.
Example Outside the Scope of the Presently Claimed Invention Example 3

Process for Recovery of 3-methyl-but-3-en-1-ol in the Presence of Isobutene

An autoclave (300 ml) was charged with 15.0 g of a (Z)-3-methylpent-2-ene-1,5-diol, (E)-3-methylpent-2-ene-1,5-diol and 3-methylenepentane-1,5-diol mixture (83 wt. %), 0.02 g urotropine and 90.0 g of isobutene. The autoclave was sealed, heated to 270° C. and stirred for 2 h at 270° C. and a pressure of 156 bar. The autoclave was cooled to 25° C. and relaxed to atmospheric pressure. The liquid single-phase residue (18.5 g) was isolated from an autoclave. Analysis by GC chromatography (wt. %) revealed the following composition:
Methanol—0.96%,
3-methyl-but-3-en-1-ol—39.2%,
(Z)-3-methylpent-2-ene-1,5-diol,
(E)-3-methylpent-2-ene-1,5-diol and
3-methylenepentane-1,5-diol mixture—17.3%.
Conversion of diol mixture—75%
Yield of 3-methyl-but-3-en-1-ol—39.3%
Selectivity of 3-methyl-but-3-en-1-ol—52.5%.

The examples clearly demonstrate that the addition of water leads to the recovery of 3-methyl-but-3-en-1-ol in higher yield with a higher selectivity.

The invention claimed is:

1. A method for recovery of 3-methyl-but-3-en-1-ol comprising at least the steps of
   a) contacting a stream comprising (Z)-3-methylpent-2-ene-1,5-diol, (E)-3-methylpent-2-ene-1,5-diol and 3-methylenepentane-1,5-diol with isobutene and water to obtain a mixture,
   b) heating the mixture obtained in step a) to a temperature in the range of ≥200° C. to ≤450° C. to obtain a treated mixture comprising 3-methyl-but-3-en-1-ol; and
   c) recovering 3-methyl-but-3-en-1-ol from the treated mixture obtained in step b).

2. The method according to claim 1, wherein the method is a continuous method.

3. The method according to claim 1, wherein the steps a) to c) are carried out simultaneously.

4. The method according to claim 1, wherein the stream comprises (Z)-3-methylpent-2-ene-1,5-diol, (E)-3-methylpent-2-ene-1,5-diol and 3-methylenepentane-1,5-diol in an amount in the range of ≥75.0 wt. % to ≤99.0 wt. %, based on the total weight of the stream.

5. The method according to claim 1, wherein the stream comprises (Z)-3-methylpent-2-ene-1,5-diol in an amount in the range of ≥15 wt. % to ≤30 wt. %, (E)-3-methylpent-2-ene-1,5-diol in an amount in the range of ≥15 wt. % to ≤30 wt. % and 3-methylenepentane-1,5-diol in an amount in the range of ≥35 wt. % to ≤55 wt. %, each based on the total weight of the stream.

6. The method according to claim 1, wherein in step a) the isobutene is added in an amount in the range of ≥75 wt. % to ≤90 wt. %, based on the total weight of the stream.

7. The method according to claim 1, wherein in step a) the water is added in an amount in the range of ≥5 wt. % to ≤70 wt. %, based on the total weight of the stream according to claim 1.

8. The method according to claim 1, wherein the step b) further comprises heating the mixture at a pressure in the range of ≥60 bar to ≤260 bar.

9. The method according to claim 1, wherein the step c) comprises at least the steps of
   A') separating the treated mixture obtained in step b) into an organic phase comprising at least ≥60 wt. % 3-methyl-but-3-en-1-ol methanol, based on the total weight of the organic phase, and an aqueous phase comprising water and ≤10 wt. % 3-methyl-but-3-en-1-ol, based on the total weight of the aqueous phase; and
   B') subjecting the organic phase obtained in step A') to a temperature in the range of ≥120° C. to ≤160° C.

10. The method according to claim 1, wherein the stream of step a) is obtained by a process comprising at least the steps of:
    A) reacting 2-methylprop-1-ene and formaldehyde to obtain a mixture comprising at least 3-methyl-but-3-en-1-ol, formaldehyde, methanol, water, (Z)-3-methylpent-2-ene-1,5-diol, (E)-3-methylpent-2-ene-1,5-diol and 3-methylenepentane-1,5-diol;
    B) separating the mixture obtained in step A) into an organic phase comprising at least 3-methyl-but-3-en-1-ol, (Z)-3-methylpent-2-ene-1,5-diol, (E)-3-methylpent-2-ene-1,5-diol and 3-methylenepentane-1,5-diol and an aqueous phase comprising water and ≤10 wt. % 3-methyl-but-3-en-1-ol, based on the total weight of the aqueous phase; and
    C) subjecting the organic phase obtained in step B) to a temperature in the range of ≥120° C. to ≤160° C. to obtain 3-methyl-but-3-en-1-ol and the stream comprising (Z)-3-methylpent-2-ene-1,5-diol, (E)-3-methylpent-2-ene-1,5-diol and 3-methylenepentane-1,5-diol.

11. The process according to claim 10, wherein in step A) the temperature is in the range of ≥200° C. to ≤350° C.

12. The process according to claim 10, wherein in step A) the pressure is in the range of ≥200 bar to ≤300 bar.

13. The process according to claim 10, wherein in step C) the pressure is in the range of ≥50 to ≤300 mbar.

14. A process for the production of 3-methyl-but-3-en-1-ol comprising the step of combining 3-methyl-but-3-en-1-ol obtained by the method of claim 1, wherein the stream of step a) is obtained by a process comprising at least the steps of:

A) reacting 2-methylprop-1-ene and formaldehyde to obtain a mixture comprising at least 3-methyl-but-3-en-1-ol, formaldehyde, methanol, water, (Z)-3-methylpent-2-ene-1,5-diol, (E)-3-methylpent-2-ene-1,5-diol and 3-methylenepentane-1,5-diol;

B) separating the mixture obtained in step A) into an organic phase comprising at least 3-methyl-but-3-en-1-ol, (Z)-3-methylpent-2-ene-1,5-diol, (E)-3-methylpent-2-ene-1,5-diol and 3-methylenepentane-1,5-diol and an aqueous phase comprising water and ≤10 wt. % 3-methyl-but-3-en-1-ol, based on the total weight of the aqueous phase; and C) subjecting the organic phase obtained in step B) to a temperature in the range of ≥120° C. to ≤160° C. to obtain 3-methyl-but-3-en-1-ol and the stream comprising (Z)-3-methylpent-2-ene-1,5-diol, (E)-3-methylpent-2-ene-1,5-diol and 3-methylenepentane-1,5-diol, with 3-methyl-but-3-en-1-ol obtained by the method according to claim 1 to obtain combined 3-methyl-but-3-en-1-ol.

15. The process according to claim 14, wherein the process further comprises the step of subjecting the combined 3-methyl-but-3-en-1-ol to a purification method to obtain combined 3-methyl-but-3-en-1-ol of a purity ≥98.0 wt. %.

* * * * *